(12) United States Patent
Xaysanasy

(10) Patent No.: US 11,089,979 B2
(45) Date of Patent: Aug. 17, 2021

(54) DEVICE AND METHOD FOR MEASUREMENT OF GLYCATED HEMOGLOBIN (A1C)

(71) Applicant: ELG Corporation, Fort Smith, AR (US)

(72) Inventor: Peter Xaysanasy, Fort Smith, AR (US)

(73) Assignee: ELG Corporation, Fort Smith, AR (US)

(*) Notice: Subject to any disclaimer, the term of this patent is extended or adjusted under 35 U.S.C. 154(b) by 171 days.

(21) Appl. No.: 16/211,278

(22) Filed: Dec. 6, 2018

(65) Prior Publication Data
US 2019/0104975 A1 Apr. 11, 2019

Related U.S. Application Data

(63) Continuation-in-part of application No. 15/809,055, filed on Nov. 10, 2017, now abandoned.
(Continued)

(51) Int. Cl.
*A61B 5/145* (2006.01)
*A61B 5/1455* (2006.01)
(Continued)

(52) U.S. Cl.
CPC ........ *A61B 5/14532* (2013.01); *A61B 5/1455* (2013.01); *A61B 5/1495* (2013.01); *A61B 5/681* (2013.01); *A61B 5/6804* (2013.01); *A61B 5/6898* (2013.01); *G16H 50/20* (2018.01); *A61B 5/0004* (2013.01); *A61B 5/02416* (2013.01); *A61B 2560/0475* (2013.01); *A61B 2562/0238* (2013.01); *G16H 40/60* (2018.01)

(58) Field of Classification Search
CPC . A61B 5/14532; A61B 5/1455; A61B 5/6804; A61B 5/681; A61B 5/6898; A61B 5/0004; A61B 5/02416; A61B 2560/0475; A61B 2562/238; A61B 1/00163; A61B 5/0059; G16H 50/20; G16H 40/60
See application file for complete search history.

(56) References Cited

U.S. PATENT DOCUMENTS 4,586,513 A * 5/1986 Hamaguri .......... A61B 5/14551
356/41
2009/0201490 A1 8/2009 Gerlitz
(Continued)

OTHER PUBLICATIONS

Timm 'Non-Invasive Haemoglobin Monitoring by an LED Based Optical Sensor System' Nov. 2010 (Year: 2010).*
(Continued)

*Primary Examiner* — Patrick Fernandes
(74) *Attorney, Agent, or Firm* — Patent Technologies, LLC; Robert D. Gunderman, Jr.

(57) ABSTRACT

A glycated hemoglobin measurement device and method is disclosed. The device provides for measurement of glycated hemoglobin (A1c) without the need for blood sampling and the associated discomfort. The device uses a 400-540 nanometer light source and associated detection circuitry to convert light returned by the source into a waveform that is then processed into a patient specific value. The determined patient specific value is then multiplied by a calibration constant to yield a glycated hemoglobin (A1c) value which is then displayed or otherwise provided to the patient or a medical practitioner.

20 Claims, 4 Drawing Sheets

Related U.S. Application Data

(60) Provisional application No. 62/420,714, filed on Nov. 11, 2016, provisional application No. 62/583,679, filed on Nov. 9, 2017.

(51) Int. Cl.

| | | |
|---|---|---|
| *A61B 5/00* | (2006.01) | |
| *A61B 5/1495* | (2006.01) | |
| *G16H 50/20* | (2018.01) | |
| *A61B 5/024* | (2006.01) | |
| *G16H 40/60* | (2018.01) | |

(56) References Cited

U.S. PATENT DOCUMENTS

2013/0164763 A1\* 6/2013 Saiki .................. G01N 33/721 435/7.25
2013/0178724 A1 7/2013 Ting et al.

OTHER PUBLICATIONS

Prabha, Comparision of the analytical techniques of hba1c estimation by immunoturbidimetric . . . , Journal, Apr.-Jun. 2017, pp. 187-190, 4(2), Int. Journ. of C. Biochem. & Res.

Pocino et al., The Hemo One Autoanalyzer for Glycated Hemoglobin Assay, Journal, 2016, pp. 119-123, 47:2, Lab Medicine.

Klose et al., Optical tomography using the time-independent equation of radiative transfer—Part 1:forward model,Journal, 2002, pp. 691-713, 72, Journal of Quant. S & RT.

Raventos et al., A method for neutron scattering quantification and correction applied to neutron imaging, Journal, Sep. 2016, pp. 275-281, 88, Elsevier B.V.

Weykamp et al., A review of the Challenge in Measuring Hemoglobin A1c, Journal, May 2009, pp. 439-445, vol. 3, Issue 3, Journal of Diabetes Science and Technology.

Baker et al., Modified Beer-Lambert law for blood flow, Journal, Oct. 28, 2014, pp. 1-23, vol. 5, No. 11, Biomedical Optics Express.

Zohdi et al., Modelling and rapid simulation of multiple red blood cell light scattering, Journal, Jul. 5, 2006, pp. 823-832, 3, Journal of The Royal Society Interface.

Higgins et al., Kinetic Analysis of the Nonenzymatic Glycosylation of Hemoglobin, Journal, May 25, 1981, pp. 5204-5208, vol. 256, No. 10, The Journal of Biological Chemistry.

Fardad et al., Scattering detection of a solenoidal Poynting vector field, Manuscript, Jul. 29, 2016, pp. 1-5, The Optical Society of America-Optics Letters.

Jacques, Optical properties of biological tissues: a review, Journal, May 2013, pp. 37-65, IOP Publishing.

\* cited by examiner

DEVICE AND METHOD FOR MEASUREMENT OF GLYCATED HEMOGLOBIN (A1C)

CROSS REFERENCE TO RELATED PATENT APPLICATIONS

This application is a continuation-in-part of application Ser. No. 15/809,055 filed on Nov. 10, 2017 entitled Apparatus and Method for Instantaneous Measuring of Glycated Hemoglobin (A1c), which claims priority to application 62/583,679 filed on Nov. 9, 2017 and application 62/420,714 filed on Nov. 11, 2016.

STATEMENT REGARDING FEDERALLY SPONSORED RESEARCH OR DEVELOPMENT

Background of the Invention

1. Field of the Invention

The present invention relates generally to medical devices, and more particularly to a device and method for measuring glycated hemoglobin (A1c) without the need for blood sampling.

2. Description of the Related Art

Diabetes mellitus is a chronic medical condition that currently affects nearly 26 million people in the United States alone. This disease is an extreme financial burden on the healthcare system in the United States as well as other countries, and is a common cause of blindness, kidney failure, complications involving the heart, blood vessels and peripheral nerves, as well as limb damage and non-traumatic limb amputation.

Glycemic control is vitally important to reducing medical complications associated with diabetes. The measurement of Hba1C (hemoglobin A1c) is a valuable metric of glycemic control. The National Glycohemoglobin Standardization Program provides for standardization of the various A1c assay techniques.

Insulin deficiency and hyperglycemia typify those patients with diabetes. As such, many pre-diabetic and diabetic patients require frequent and ongoing monitoring of glycated hemoglobin throughout medical treatment of their condition. This typically involves the pricking of a finger to obtain a blood sample that can be used for subsequent testing of blood glucose levels by way of measurement of A1c levels. Repetitive blood sampling for assay purposes presents not only pain to the patient, but also sanitary and safety concerns. What is therefore needed is a non-invasive device for the measurement of glycated hemoglobin (A1c) that does not require blood sampling.

BRIEF SUMMARY OF THE INVENTION

In accordance with the present invention, there is provided a glycated hemoglobin measurement device and related methods. The device comprises a source of light having a wavelength in the range of 400 nanometers to 540 nanometers, a light detector capable of detecting light having a wavelength between 400 nanometers and 540 nanometers and configured to output a time variant voltage that corresponds with the amount of light detected, a housing configured to receive an anatomical body part of a patient, the source of light placed within the housing and configured to irradiate at least a portion of the anatomical body part received by the housing, the light detector placed within the housing and configured to receive reflected light returning back from the irradiated anatomical body part of the patient, an analog to digital converter configured to receive the time variant output voltage of the light detector and convert the time variant output voltage to a binary representation, a computer having a processor, memory, and access to computer readable media, an interface configured to receive the binary representation of the time variant output voltage from the analog to digital converter, a computer program stored on the computer readable media where the computer program executes the steps of: retrieving the binary representation of the time variant output voltage, averaging the binary representation of the time variant output voltage across a specified time t to yield an average voltage, multiplying the average voltage by a constant K to yield a glycated hemoglobin equivalent, wherein the constant K is retrieved from a calibration data table stored on the computer readable media, and displaying on a visual indicator the resulting glycated hemoglobin equivalent.

The foregoing has been provided by way of introduction, and is not intended to limit the scope of the invention as described by this specification, claims, and the attached drawings.

BRIEF DESCRIPTION OF THE DRAWINGS

The invention will be described by reference to the following drawings, in which like numerals refer to like elements, and in which.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention as defined by this specification, claims, and drawings attached hereto.

DESCRIPTION OF THE PREFERRED EMBODIMENTS

As will be further described herein, a device and related methods for the non-invasive measurement of glycated hemoglobin is disclosed. Without wishing to be bound to any particular theory or theories, the following disclosure is provided. With the present invention, light having a wavelength in the range of 400 to 540 nanometers is irradiated upon an anatomical body part, with a portion of the irradiated light being absorbed by various anatomical components including hemoglobin, and a portion of the irradiated light being reflected and in turn received by a detector. The detector with associated circuitry then provides a waveform that undergoes signal processing to yield an average signal value that is multiplied by a calibration value to in turn output an A1c value. The device, signal processing and methods to generate the calibration values are further described by way of the following specification and drawings appended herein.

Figure 1:
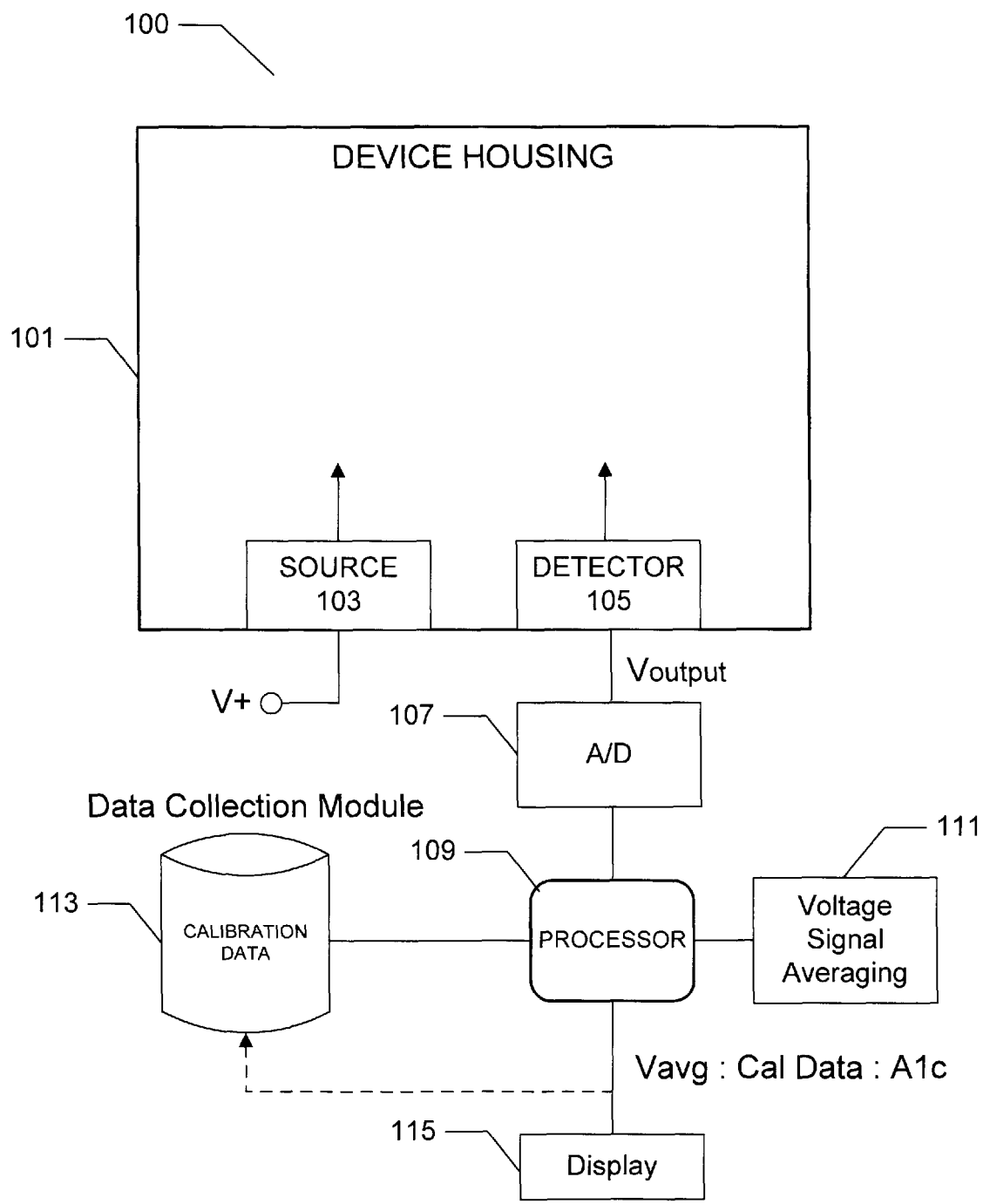
FIG. 1 depicts a block diagram of the main constituent components of the glycated hemoglobin measurement device of the present invention.

Turning first to FIG. 1, a block diagram of the main constituent components of the glycated hemoglobin measurement device 100 of the present invention can be seen. A device housing 101 accommodates the electronics and also provides a receptacle or other such fixture to receive an anatomical body part. The anatomical body part to be received by the device may include a thumb, a finger, a fingertip, a toe, or other such patient extremity that will allow for the transmission of light through the skin of a patient. The device housing 101 may, in some embodiments of the present invention, be a personal item such as a smart phone, a watch, a device with a wrist strap, a device with a chest strap, a portable electronic device, a device with an ankle strap, a stand-alone device, a networked device, or a clothing item. Such a personal item may include the device of the present invention, or be networked or otherwise connected to the device using a wired or wireless connection. The device housing 101 may also include a shroud, shield, or similar entry structure that accommodates and optically and electrically shields a patient's anatomical extremity (thumb, finger, earlobe, toe, and the like). A source of optical radiation 103 such as a light emitting diode is situated within or upon the device housing in such a way that the source is capable of emitting light into a patient extremity, such as a thumb, fingertip, or the like. The light emitted by the source 103 has a wavelength in the range of 400 to 540 nanometers. In some embodiments of the present invention, the emitted light may be continuous, pulsed, multiplexed, phase shifted, or further processed or modified. The light source 103 directs emitted light into the patient extremity, where a portion of the directed or emitted light is absorbed by the extremity and by the blood therein, and a portion of the emitted light is reflected back out of the extremity and received by a detector 105. The detector 105 is configured to receive light in the range of 400 to 540 nanometers and is further configured to provide an output of the received light in a waveform or other such signal that may be voltage based or current based. The detector 105 may be made from a variety of materials that are sensitive to incident photons, such as Silicon, Gallium Arsenide, Cadmium Sulfide, Cadmium Zinc Telluride, and the like. CCD devices, quantum dot devices, graphene devices, and other such detectors may also be employed. The detector 105 may also include additional circuitry such as amplifiers, transistors, capacitors, resistors, and the like to provide a useful output signal that can be further processed. In some embodiments of the present invention, the source 103 and the detector 105 are coplanar in the device housing 101, meaning that the two elements are adjacent to each other to allow for the reception of reflected light from the source 103 by the detector 105. The time variant output signal from the detector 105 is then received by an analog to digital converter 107 or the like. With the analog to digital converter 107, the time variant output signal from the detector 105 is converted to a binary or similar digital representation to allow for further processing by way of a microprocessor 109 and related components (such as memory, registers, multiplexers, demultiplexers, I/O devices, and the like). The time variant output signal from the detector 105 is periodic where the time period is related to patient heart rate. In one embodiment of the present invention, the time variant output signal is a sawtooth wave with an amplitude in the range of zero to 1.2 volts. The processor 109 will average the voltage signal through a voltage signal averaging function 111 and provide a numerical output that is proportional to the average voltage of the output signal. In one embodiment of the present invention, the average voltage of the output signal is taken at each period of the output waveform, thus providing a plurality of average voltage values. The average voltage values are then multiplied by a calibration value or values to yield a value that corresponds with percentage of A1c of the patient. The calibration values are contained in memory in the form of calibration data 113, and are obtained through methods of the present invention that will be further described herein. The resulting A1c values are provided on a display 115 such as an LED or LCD display, a computer monitor, a smart phone display, or the like. Additionally, the patient's resulting A1c values may be transmitted, collected, stored, and further processed through additional functionality including additional devices, networks, processors, or such. Additional functionality may also be provided that further relates patient A1c values to blood glucose.

The resulting A1c values are not limited to a visual representation through the display 115, but may be stored in computer memory, transmitted to another electronic device through wired or wireless connections, provided to a centralized data repository for further processing, calibration improvements, patient specific or patient group studies, or the like.

Figure 2:
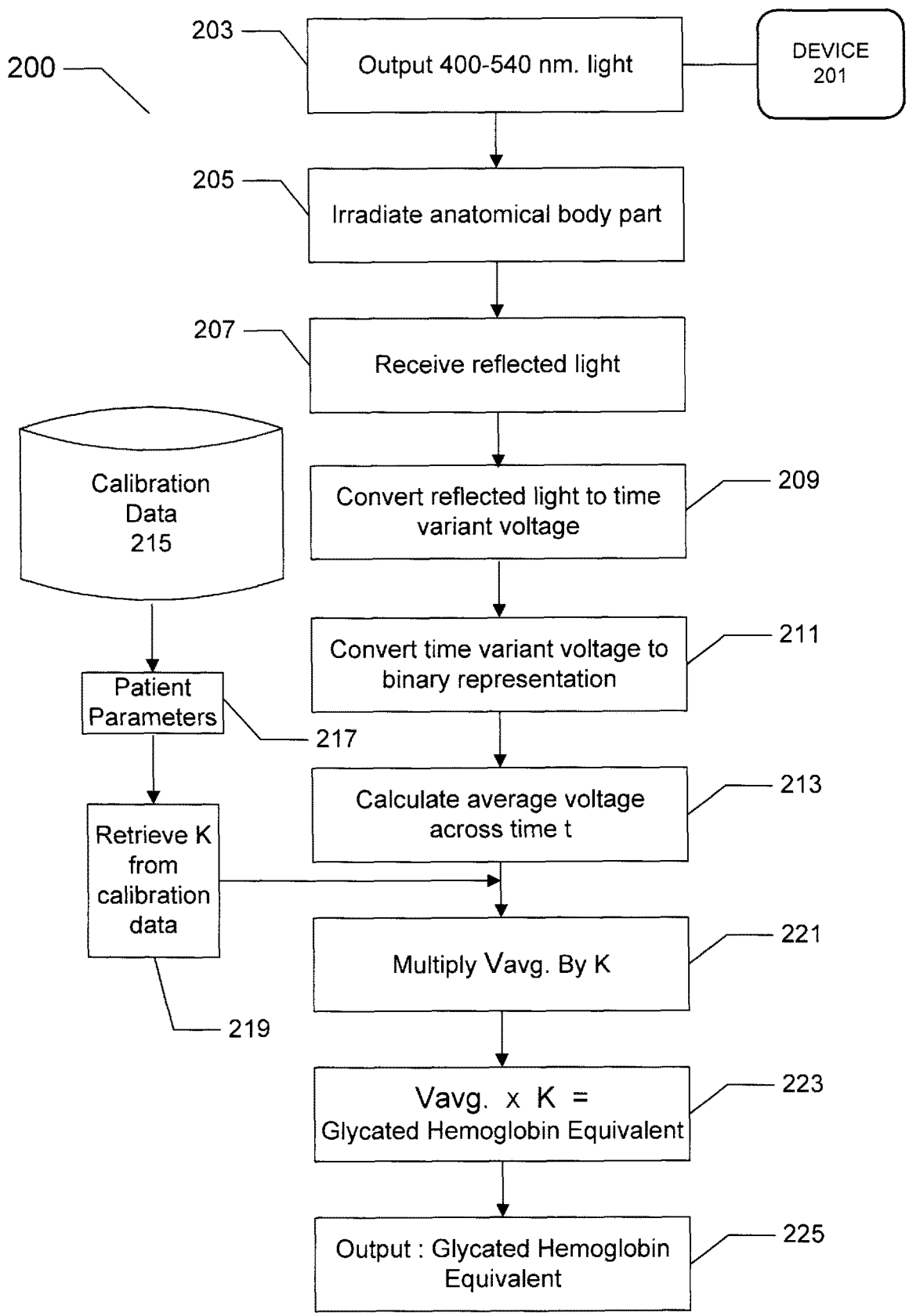
FIG. 2 is a flowchart of steps performed by the glycated hemoglobin measurement device of the present invention.

Turning now to FIG. 2, a flowchart 200 of steps performed by the glycated hemoglobin measurement device of the present invention is depicted.

The device 201 provides a light source in the range of 400-540 nm. where the output in step 203 irradiates an anatomical part of a patient in step 205. The incident light penetrates at least a portion of the anatomical body part of the patient, with some of the incident light being absorbed and some of the incident light being reflected. The reflected light is then received in step 207 by a detector, as previously described. This reflected light, as received by the detector, is then converted to a time variant signal, such as a time variant voltage in step 209. This conversion is performed by way of a voltage being applied to the detector in such a way that the resulting output of the detector (the time variant signal) is proportional to a change in physical properties of the detector. This change in physical property may be a change in resistance, a change in voltage or current characteristics, or the like. It should be noted that the time variant nature of the resulting output of the detector can be attributed to patient heart rate, where the pulsation of blood flow due to heart rhythm results in time variant detection characteristics.

To facilitate processing of the detector output, the time variant output of the detector, an analog signal, is converted to a binary or digital representation in step 211. Such conversion is performed by way of, for example, an analog to digital converter. Once the time variant output signal from the detector is converted to a digital or binary representation, an average voltage of the output signal can be calculated. In one embodiment of the present invention, the analog representation of the output signal resembles a sawtooth or triangle-type waveform. In step 213, an average voltage of the output waveform is determined over a time period t, where t is specified and may be repetitive, allowing for near real time sampling and A1c readings. A microprocessor with memory and access to computer readable media is used to calculate average voltage values. Once an average voltage value is calculated for a specified time period t, a constant K is retrieved from a source of calibration data and multiplied with the average voltage value in step 223, resulting in a value for glycated hemoglobin equivalent.

The source of calibration data 215 may be a database, a network, computer readable media, computer memory, or the like. The calibration data comprises A1c readings from finger prick studies, and may further be sorted, organized, or otherwise delineated by patient parameters 217. These patient parameters may include, for example, age, weight, sex, race, or the like. A constant K is retrieved from the calibration data 215 in step 219 and used in steps 221 and 223 (as previously described), resulting in an output in step 225 that represents Glycated Hemoglobin Equivalent for the patient. This output may be represented on a display, another device such as a smart phone or computer, or the like.

The output displayed represents A1c, also known as glycated hemoglobin, glycosylated hemoglobin, hemoglobin A1c, and HbA1c, is provided as a percentage, specifically what percentage of the patient's hemoglobin is coated with sugar (glycated). A1c percentages provide information on a diagnosis of diabetes as well as how well a patient is managing their blood sugar. Traditional A1c testing involves taking a blood sample, with the A1c level (a percentage) corresponding to the patient's estimated average blood sugar level (commonly expressed in milligrams per deciliter or millimoles per liter). A1c testing reflects a patient's average blood sugar level for the past two to three months.

It is important that the device of the present invention incorporate calibration data to ensure that the measurements made are accurate. The measurements made with the device of the present invention involve the use of a spectroscopy technique that employs light in the 400-540 nm. wavelength range and a resulting output signal and related signal processing. The calibration data 215 contains A1c percentages for specific patient populations as determined by traditional blood sampling techniques. Overlaid on the blood sampling data are average voltage values for output voltages from the detector of the present invention. Thus, calibration data is to created through patient sampling where an A1c value is determined by way of a traditional blood draw test, with the patient then employing the device of the present invention to determine an average voltage value from the detector 105 that can be assigned to that A1c value. These co-relational tests may be performed more than once, and may also be performed on specific groupings or classes of patients. Thus, calibration data that relates blood sampled A1c percentages to average voltage values from the device of the present invention is cumulatively stored as calibration data in a database or similar memory. This calibration data provides for a constant K that is multiplied by the average voltage value of a new reading to yield a glycated hemoglobin equivalent percentage, as displayed on the device of the present invention. As will be further described by way of FIG. 3, the continued addition of data from these correlational tests provides for ever-improving A1c readings from the device of the present invention.

Figure 3:
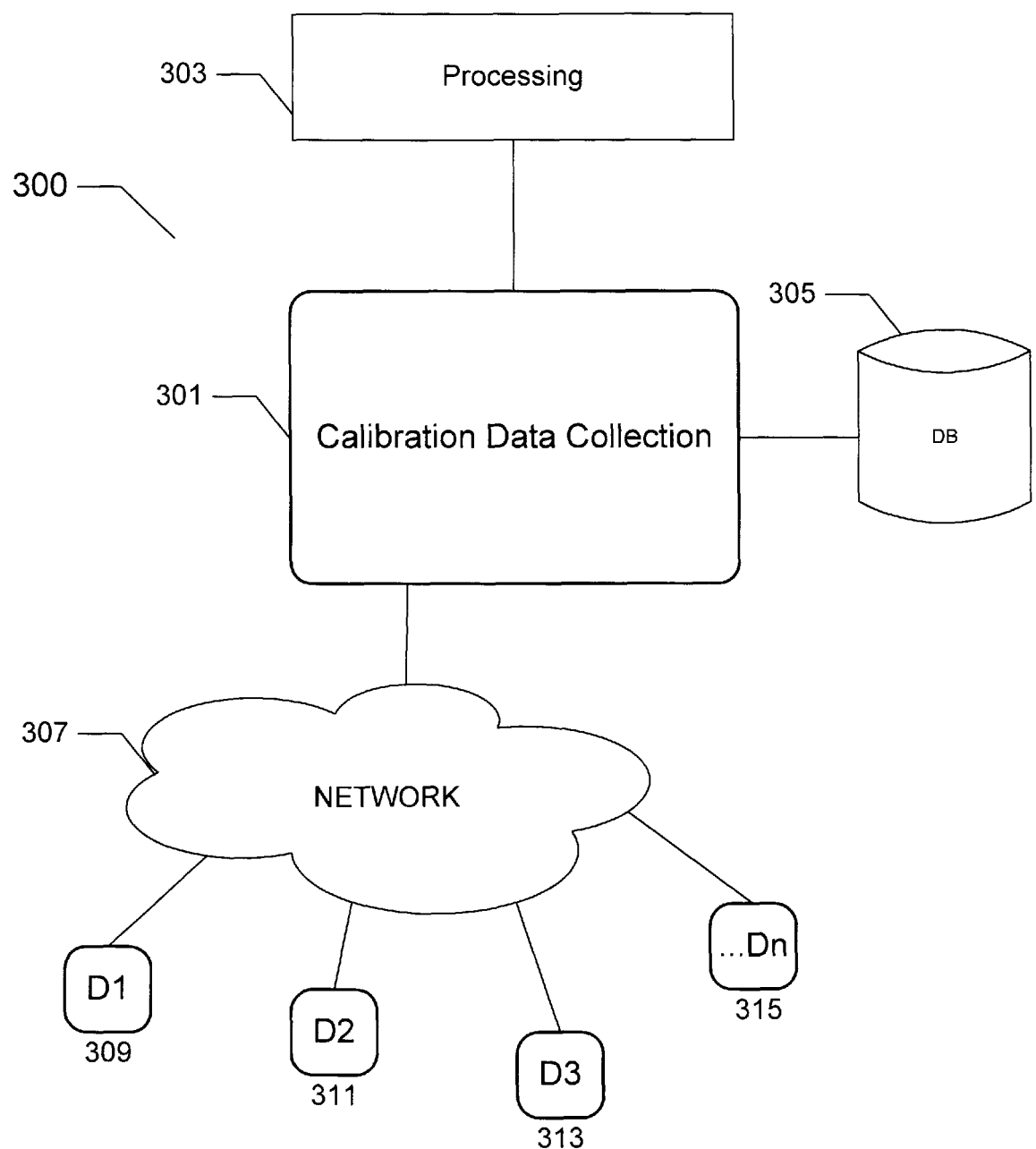
FIG. 3 is a diagram of a calibration network of the present invention.

FIG. 3 depicts a diagram of a calibration network 300 of the present invention. Calibration data collection 301 may be at the device level, or may comprise connectivity to a network 307 where a plurality of devices D1 . . . Dn, 309-315 are used to collect optical based A1c measurements from the device of the present invention and also to collect correlational A1c percentages from blood sampling tests. This calibration data may be sent over a network 307 to a calibration data collection point, location, system, or the like, and then stored in computer memory such as a database 305. The collected calibration data may then undergo further processing 303 such as sorting, aggregating, consolidating, parsing, editing, or the like. Calibration data may also be sorted by patient profile, race, color, sex, height, weight, or the like.

While the term calibration data may outwardly appear to indicate data that may be fixed or otherwise referenced to a standard that is non-changeable, calibration data as used herein refers to data that is collected from various sources and used to improve the accuracy of the device readings. This data collection and resulting calibration data may be ongoing as the device is deployed and used. Such ongoing data collection and processing not only improves patient specific device accuracy, but also improves the accuracy of entire groups or classifications of patients. It should be noted that the value K that is obtained from the calibration data and multiplied by the average output voltage of the detector 105 (see FIG. 1) may be a constant that is linear throughout the range of A1c percentages for a patient, but may also represent a non-linear relationship that requires multiple calibration data values throughout an A1c percentage range. This non-linear relationship may be further defined by not only patient specific characteristics, but also by variables that exist with different patient classifications. For example, skin pigmentation or age may impact the optical characteristics of the patient's skin, providing for different K values and profiles with different skin types. With larger calibration data population sets, such differences may be identified and integrated with K value calculations.

Figure 4:
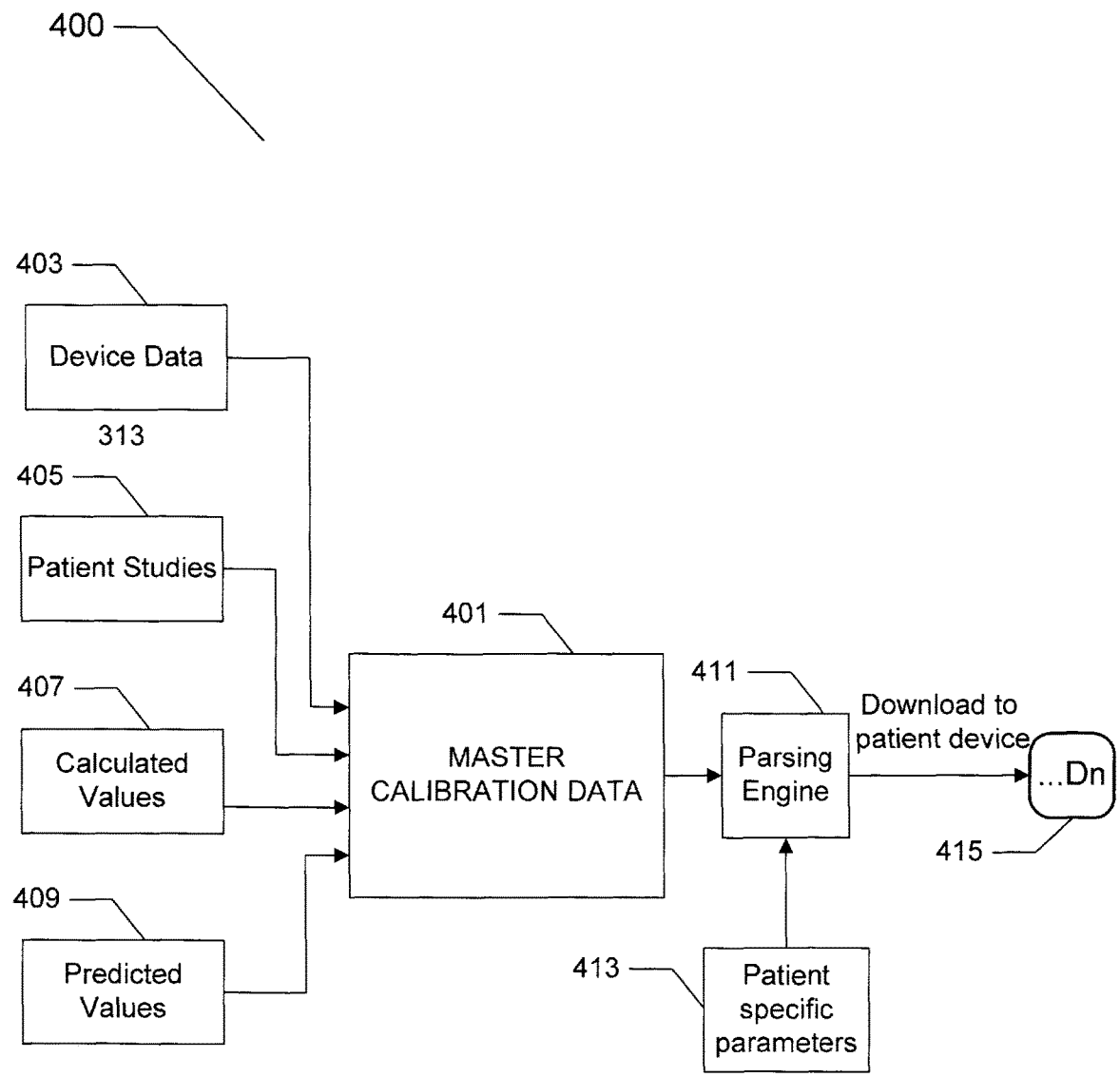
FIG. 4 is a data flow diagram depicting device calibration.

FIG. 4 depicts a data flow diagram of device calibration.

To achieve ongoing device accuracy, co-relational device data 403 from a plurality of devices may be collected and processed in a set or sets of master calibration data 401. In addition, patient studies 405 may be performed on various sets and sub-sets of patients to continue to build master calibration data 401. Calculated values 407 that are determined through empirical testing, laboratory analysis, and the like may also contribute to the master calibration data 401. Predicted values 409 based on refined or predicted calculations, formulas, and theory may also contribute to the master calibration data. As data collection continues over time, additional equations and formulas may be developed that further define the K values needed for glycated hemoglobin equivalent output at the device level. The master calibration data 401 may reside in computer based memory and may be organized in a database for ease of manipulation, processing and access. A parsing engine 411 may be employed to divide the master calibration data 401 into meaningful sets or groups. Patient specific parameters 413 such as age, race, skin type, sex, body mass index, weight, and the like may also be used with the parsing engine 411 to create patient specific calibration data that can be download to a patient device 415. The calibration data may be periodically updated or refreshed at the device level to ensure that the device is providing accurate A1e percentage readings. The A1c readings, as previously stated, may be stored and transferred back to the set of master calibration data 401. Over time, with increases in calibration data size, the device will continue to improve in diagnostic capabilities across a broad range of patient types. As such, the master calibration data improves as the quantity of data collected and stored there within increases.

It is, therefore, apparent that there has been provided, in accordance with the various objects of the present invention, a device and method for the measurement of glycated hemoglobin (A1c).

While the various objects of this invention have been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of this specification, claims and drawings appended herein.

What is claimed is:

1. A glycated hemoglobin measurement device comprising:
    a source of light having a wavelength in the range of 400 nanometers to 540 nanometers;
    a light detector configured to detect light having a wavelength between 400 nanometers and 540 nanometers and configured to output a time variant voltage that corresponds with an amount of light detected;
    a housing configured to receive an anatomical body part of a patient;
    the source of light placed within the housing and configured to irradiate at least a portion of the anatomical body part received by the housing;
    the light detector placed within the housing and configured to receive reflected light returning back from the irradiated anatomical body part of the patient;
    an analog to digital converter configured to receive the time variant voltage of the light detector and convert the time variant voltage to a binary representation;
    a computer having a processor, a memory, and access to non-transitory computer readable media;
    an interface configured to receive the binary representation of the time variant voltage from the analog to digital converter;
    a computer program stored on the non-transitory computer readable media where the computer program executes the steps of:
    retrieving the binary representation of the time variant voltage;
    averaging the binary representation of the time variant voltage across a time t to yield an average voltage;
    multiplying the average voltage by a constant K to yield a glycated hemoglobin equivalent;
    wherein the constant K is retrieved from a calibration data table containing A1c readings from finger prick studies stored on the non-transitory computer readable media; and
    displaying on a visual indicator the glycated hemoglobin equivalent;
    wherein the constant K is determined based on data stored in the calibration data table.

2. The glycated hemoglobin measurement device of claim 1, wherein the source of light and the light detector are coplanar in the housing.

3. The glycated hemoglobin measurement device of claim 1, wherein the anatomical body part of a patient is a thumb.

4. The glycated hemoglobin measurement device of claim 1, wherein the anatomical body part of a patient is a finger.

5. The glycated hemoglobin measurement device of claim 1, wherein the housing is a personal item.

6. The glycated hemoglobin measurement device of claim 5, wherein the personal item is selected from the group consisting f a watch wrist, strap, a chest strap, a smart phone, a portable electronic device, an ankle strap, or a clothing item.

7. The glycated hemoglobin measurement device of claim 1, wherein the calibration data table is patient specific.

8. The glycated hemoglobin measurement device of claim 1, wherein the calibration data table is compiled from patient studies.

9. The glycated hemoglobin measurement device of claim 1, wherein the calibration data able periodically updated based on ongoing patient specific measurements.

10. The glycated hemoglobin measurement device of claim 1, wherein the calibration data table is periodically updated based on additional patient studies.

11. The glycated hemoglobin measurement device of claim 1, further comprising a data collection module.

12. The glycated hemoglobin measurement device of claim 11, wherein the data collection module stores glycated hemoglobin measurements taken by the glycated hemoglobin measurement device.

13. A glycated hemoglobin measurement device comprising:
    a source of light having a wavelength in the range of 400 nanometers to 540 nanometers;
    a light detector configured to detect light having a wavelength between 400 nanometers and 540 nanometers;
    the source of light and the light detector being coplanar in a housing to allow for the detection of reflected light by the light detector;
    the housing configured to receive an anatomical body part of a patient;
    an electrical circuit to convert detected light to a numerical value;
    the numerical value being representative of a glycated hemoglobin value;
    a computer having a processor, a memory, and access to non-transitory computer readable media;
    a computer program stored on the non-transitory computer readable media where the computer program executes the steps of:
    retrieving the numerical value;
    multiplying the numerical value by a constant K to yield a glycated hemoglobin equivalent;
    wherein the constant K is retrieved from a calibration data table containing A1c readings from finger prick studies stored on the non-transitory computer readable media; and
    displaying on a visual indicator the glycated hemoglobin equivalent;
    wherein the constant K is determined based on data stored in the calibration data table.

14. The glycated hemoglobin measurement device of claim 13, wherein the housing is a personal item.

15. The glycated hemoglobin measurement device of claim 14, wherein the personal item is selected from the group consisting f a watch, a wrist strap, a chest strap, a smart phone, a portable electronic device, an ankle strap, or a clothing item.

16. The glycated hemoglobin measurement device of claim 13, further comprising a data collection module.

17. The glycated hemoglobin measurement device of claim 13, wherein the anatomical body part of a patient is a thumb.

18. A method for determining a glycated hemoglobin value comprising the steps of:
    detecting, on a computer having a processor, a memory and access to non-transitory computer readable media, a time variant output signal from a light detector wherein the light detector is configured to detect light having a wavelength in the range of 400-540 nanometers;
    converting on an analog to digital converter the time variant output signal to a binary representation;

averaging on the computer the binary representation of the time variant output signal across a time t to yield an average voltage;

multiplying on the computer the average voltage by a constant K to yield a glycated hemoglobin equivalent;

wherein the constant K is retrieved from a calibration data table containing A1 c readings from finger prick studies stored on the non-transitory computer readable media; and displaying on a visual indicator the glycated hemoglobin equivalent;

wherein the constant K is determined based on data stored in the calibration data table.

19. The method of claim 18, further comprising the step of:

improving the calibration data table by adding ongoing patient specific measurements.

20. The method of claim 18, further comprising the step of:

improving the calibration data table by adding additional patient studies.

* * * * *